United States Patent [19]

Smith et al.

[11] Patent Number: 5,194,417

[45] Date of Patent: Mar. 16, 1993

[54] PRETREATMENT OF PALLADIUM-GOLD CATALYSTS USEFUL IN VINYL ACETATE SYNTHESIS

[75] Inventors: David W. Smith, Cincinnati; Ronnie M. Hanes, Loveland, both of Ohio; John A. Scheben, Erlanger, Ky.; Steve M. Augustine, Cincinnati, Ohio

[73] Assignee: Quantum Chemical Corporation, New York, N.Y.

[21] Appl. No.: 802,653

[22] Filed: Dec. 5, 1991

[51] Int. Cl.$^5$ .......................... B01J 23/52; B01J 23/44
[52] U.S. Cl. ...................................... 502/330
[58] Field of Search .......................... 502/330

[56] References Cited

U.S. PATENT DOCUMENTS

| | | | |
|---|---|---|---|
| 3,142,713 | 7/1964 | Carr et al. | 502/50 X |
| 3,480,558 | 11/1969 | Lum et al. | 502/50 |
| 3,743,607 | 7/1973 | Sennewald et al. | 502/170 |
| 3,879,311 | 4/1975 | Schott et al. | 502/26 |
| 3,917,676 | 11/1975 | Kisaki et al. | 502/207 X |
| 4,048,096 | 9/1977 | Bissot | 502/170 |
| 4,087,622 | 5/1978 | Nakamura et al. | 502/170 X |
| 4,093,559 | 6/1978 | Fernholz et al. | 502/170 |
| 4,136,062 | 1/1979 | Boudart et al. | 502/330 X |
| 4,188,490 | 2/1980 | Hinnenkamp et al. | 560/245 |
| 4,370,261 | 1/1983 | Wunder et al. | 502/328 |
| 4,490,481 | 12/1984 | Boitiaux et al. | 502/330 |
| 4,551,442 | 11/1985 | Pesa et al. | 502/330 X |
| 4,621,071 | 11/1986 | Blanchard et al. | 502/302 |
| 4,816,434 | 3/1989 | Simpson | 502/210 |
| 4,902,823 | 2/1990 | Wunder et al. | 560/245 |

*Primary Examiner*—W. J. Shine
*Assistant Examiner*—Douglas J. McGinty
*Attorney, Agent, or Firm*—Kenneth D. Tremain; William A. Heidrich

[57] ABSTRACT

A method for pretreatment of a palladium-gold catalyst useful in the synthesis of vinyl acetate. A virgin catalyst, following reduction to the metallic palladium and gold, is first heated at elevated temperatures in the presence of an oxidizing agent such as air. The oxidizing agent is withdrawn and an inert gas such as nitrogen is introduced. The catalyst is heated against at a temperature up to 500° C. in the presence of a reducing agent such as hydrogen or ethylene. Improvement in selectivity and yield are obtained.

13 Claims, No Drawings

PRETREATMENT OF PALLADIUM-GOLD CATALYSTS USEFUL IN VINYL ACETATE SYNTHESIS

BACKGROUND OF THE INVENTION

1. Field of the Invention

This invention relates to the manufacture of vinyl acetate using a catalyst comprising palladium and gold. More particularly, the invention is directed to a method for pretreating a metallic palladium-gold catalyst by sequential oxidation and reduction steps.

2. Discussion of the Art

The process of employing palladium-gold catalysts to obtain vinyl acetate from ethylene, acetic acid, and oxygen has been known for decades. Such catalysts are discussed by Sennewald et al in U.S. Pat. No. 3,488,295 and U.S. Pat. No. 3,743,607, and by Nakamura et al. in U.S. Pat. No. 4,087,622.

The catalytic elements in palladium-gold systems are in substantially metallic form, although some oxides may be present at the surface. Gold is typically present in minor amounts relative to the amount by weight of palladium. These expensive metals are deposited in relatively minor amounts on the surface of a support material or a carrier such as silica, alumina, or other materials. Examples of support materials are given by Bartsch in U.S. Pat. No. 4,158,737 and by Wunder et al. in U.S. Pat. No. 4,902,823.

There are various methods for depositing the palladium and gold on the carrier surface. One is described in U.S. Pat. No. 3,917,676 to Kisaki et al where in Example 1 a palladium salt is first dissolved, an alumina carrier is impregnated with that solution, the coated carrier is dried in air at 250° C., and palladium metal is finally obtained by reducing with hydrogen at 200° C. It is also possible, as mentioned in U.S. Pat. No. 4,087,622 to Nakamura and in U.S. Pat. No. 3,917,676 to Kisaki, to heat the metal salt to cause the corresponding oxide to be formed in situ on the support, and then to reduce the oxide to form the metal.

These and similar methods of catalyst preparation which involve sequential oxidation and reduction of metal salts to manufacture a catalyst in metallic form are to be distinguished from the present invention for pretreatment in which a finished catalyst, already in metallic form, is then subjected to the oxidation and reduction treatment of the invention.

Procedures used to regenerate spent catalysts must also be distinguished. It is well known that vinyl acetate catalysts will eventually decline in activity to a point where it becomes economic to regenerate the catalyst and/or replace it with fresh catalyst. Lum and Mador in U.S. Pat. No. 3,480,558 teach the regeneration of a spent palladium catalyst by sequential treatment with oxygen and hydrogen to remove organic residues from the catalyst. There is no suggestion that such treatment of a virgin catalyst would have any beneficial effect.

It is an object of this invention to achieve a catalyst with improved initial selectivity to vinyl acetate while maintaining a high conversion. It is also an object to reduce the frequency of regeneration or replacement of the catalyst.

SUMMARY OF THE INVENTION

The invention concerns a method for the pretreatment of a virgin catalyst comprising metallic palladium and gold. The catalyst is first heated for at least 15 minutes, at a temperature at least sufficient to partially oxidize the palladium, in the presence of an oxidizing agent such as air. The oxidizing agent is withdrawn and an inert gas such as nitrogen is introduced. The catalyst is heated again at a temperature up to 500° C. for at least 15 minutes in the presence of a reducing agent such as hydrogen or ethylene.

DETAILED DESCRIPTION OF THE INVENTION

The invention described in detail here is directed to a pretreatment for improving the performance of palladium-gold catalysts as are used in the manufacture of vinyl acetate.

Catalyst

The catalyst to be pretreated comprises palladium and gold in reduced metallic form, as individual metals or in alloys or both. In these catalysts the palladium is present at 0.1 to 5 percent based on the weight of the completed catalyst including support material, while the gold is present at 0.1 to 2 percent. It is permissible and sometimes unavoidable that very minor amounts of the palladium will be present in the oxide form, particularly at surface layers of the metal. The catalyst can be supported on a carrier and can optionally contain additional elements as activators or promoters, as is common in the art.

By "virgin catalyst" is meant that the catalyst preparation has been completed but the catalyst has not yet been used. At this point substantially all of the palladium and gold have been reduced to metal from their precursor compounds or complexes, leaving no more than five, and preferably less than one, weight percent of an element in a non-metallic form. Also at this point the catalyst has not been subjected to the combination of ethylene and oxygen for any significant time, preferably less than two hours, most preferably not at all.

Pretreatment

In the pretreatment method, the virgin catalyst described above is exposed first to an oxidizing agent at conditions sufficient to at least partially oxidize the palladium metal. The oxidizing agent can be selected from oxygen, nitrogen oxides, nitrate salts, and hydrogen peroxide.

In a preferred embodiment, the oxidizing agent is an oxygen-containing gas. The virgin catalyst is exposed to this gas at a temperature sufficient to at least partially oxidize the palladium metal but below that which would damage the catalyst. Temperatures are preferably from 125° C. to 500° C., more preferably between 150° and 350° C., and most preferably between 200° and 300° C. The catalyst should be maintained at this temperature for at least 15 minutes; a recommended time is between one and eight hours. The optimum time will vary depending on the final temperature, the amount of oxygen, and the temperature at which the pretreatment gas is introduced.

For economic reasons, air or air diluted with additional nitrogen is preferred as the oxygen-containing gas, although other gas mixtures can be used. Ethylene and other combustible materials are absent. The oxygen content can range from 1 to 100 percent, preferably from 1 to 50%, most preferably from 4 to 25%. A stoichiometric excess of oxygen is preferred relative to the amount of palladium in the catalyst to assure sufficient contact with the metals in the catalyst.

In the second step the oxidizing agent is withdrawn and an inert gas is introduced. Nitrogen is the preferred inert gas, but others such as carbon dioxide, helium, and argon are also suitable. A primary purpose of the inert gas is to purge the catalyst environment of oxygen to avoid explosive ranges. The temperature of the catalyst and the inert gas during the second step is less critical provided it remains below that which would damage the catalyst, i.e., below about 500° C. The temperature can be increased, or maintained at the ending temperature of the first step, or be allowed to return to ambient before or during the flow of inert gas.

In the third step the catalyst is treated in a reducing environment at a temperature from ambient or sub-ambient up to 500° C, preferably from 100° to 500° C, most preferably about 150° to 350° C. The reducing agent can include, for example, ammonia, carbon monoxide, hydrogen, aldehydes, alcohols, olefins, primary amines, and formic acid or salts thereof. Preferred agents are selected from the group consisting of hydrogen, ethylene, propylene, methanol, and formaldehyde. Preferred among these are hydrogen and ethylene. Mixtures of these can also be used, and they can be diluted with other gases, preferably inert. Treatment times are in the same ranges as recommended for the oxidizing agent.

In an alternate embodiment of the invention, the oxidizing and/or reducing agents can also be fed while heating the catalyst from ambient to the treatment temperature.

The same reactor vessel used for the manufacture of vinyl acetate can be used for the pretreatment, as can any other vessel capable of subjecting the catalyst to the pretreatment conditions. The pretreatment is preferably conducted at atmospheric or an elevated pressure, but may also be conducted at subatmospheric pressure.

The invention is further illustrated by reference to the following examples.

EXAMPLES

Comparison A

A large batch of a conventional catalyst containing nominally 1 percent palladium and 0.5 percent gold and supported on alpha-alumina, referred to as batch lot A, was prepared using conventional methods but was not pretreated by the method of this invention. Two hundred grams of catalyst from lot A were tested in the vinyl acetate synthesis reaction at 125° C., 35 psig, and standard liters/hour of 51.9 ethylene, 5.6 oxygen, 12.0 acetic acid, 2.1 water, and 2.4 nitrogen. The vinyl acetate yield, selectivity, and oxygen conversion were determined as shown in Comparison A in the Table.

Example 1

In this example, the catalyst is treated throughout the heating stage. From the same batch lot A used above, 100 pounds of virgin catalyst were pretreated in an air flow (at one atmosphere, 50 SCF/hr) while heating from ambient to 300° C. over a 4.5 hour period. The temperature was then held at 302°-307° C. for three hours, after which the catalyst was cooled to room temperature. After flushing with nitrogen, the catalyst was then subjected to a mixture of 50% hydrogen and 50% nitrogen at one atmosphere and 35.4 SCF/hr while heating from ambient to 350° C. over a period of 6.5 hours. The temperature was held from 346 to 349° C. for three hours, and the catalyst was then cooled to room temperature under the same hydrogen/nitrogen atmosphere. Two hundred grams of this catalyst were tested in the vinyl acetate synthesis reaction at the same conditions as in Comparison A, and the vinyl acetate yield, selectivity, and oxygen conversion were determined as shown in Example 1 in the Table.

Example 2

In this example, the catalyst is first heated and then subjected to the treating gases. From the catalyst lot used for Comparison A, 100 pounds of virgin catalyst were heated to 250° C. under a flow of nitrogen. The nitrogen was then replaced by an air flow (at one atmosphere, 50 SCF/hr) while the temperature was maintained at 250° C. for 3 hours. The air feed was stopped and a nitrogen purge started while still maintaining temperature. Then a flow of 25% hydrogen and 75% nitrogen at one atmosphere and 23.6 SCF/hr was begun and maintained for 3 hours. Hydrogen flow was discontinued and the catalyst was then cooled to room temperature under nitrogen flow. 200 grams of this catalyst were tested in the vinyl acetate synthesis reaction as in Comparison A, with data reported as Example 2 in the Table.

Comparison B

A second batch of untreated catalyst, similar but not identical to lot A above, was obtained as batch lot B. Twenty-five grams of this catalyst were tested in the vinyl acetate synthesis reaction at 135° C, 35 psig, and mole/hour feeds of 0.6B ethylene, 0.076 oxygen, 0.16 acetic acid, 0.03 water, and 0.32 nitrogen. Data from this Comparison B are shown in the Table.

Example 3

In this example, the catalyst is first heated and then subjected to the treating gases using a bench-scale unit. From catalyst lot B, 113.3 grams (100cc) of virgin catalyst were heated to 200° C. at 2 C/minute under nitrogen flow (330 SCCM/minute) at 30 psig. The nitrogen was stopped and the reactor was vented. Air was fed in at 30 psig (670 SCCM/minute) for three hours while the temperature was maintained at 200° C. Air was replaced by nitrogen purge for one hour at the former conditions for nitrogen. Then hydrogen was co-fed (330 SCCM/min) with the nitrogen maintaining temperature and 30 psig pressure for three hours. Hydrogen flow was discontinued and the catalyst was then cooled to room temperature under nitrogen flow. This catalyst was tested in the vinyl acetate synthesis reaction at the conditions of Comparison B, and data are presented as Example 3 in the Table.

Example 4

The procedure of Example 3 was followed except that the treatment temperature was 250° C., pressure was 80 psig, and hydrogen co-feed was 50 SCCM/minute.

Example 5

A variation of the procedure of Example 3 was used. From catalyst lot B, 200.4 grams of virgin catalyst were heated to 250° C. at 10° C./minute under nitrogen flow (330 SCCM/minute) at atmospheric pressure. The nitrogen was stopped. Air was then fed in at atmospheric pressure and 670 SCCM/minute for four hours while the temperature was maintained at 250° C. Air was replaced by nitrogen and the catalyst temperature was raised to 350° C. at 10° C./minute. At 350° C., a mixture of 333 SCCM/min each of nitrogen and hydrogen were fed for 15 minutes, after which hydrogen flow was stopped. The catalyst was then cooled to room temperature under nitrogen flow. This catalyst was tested in the vinyl acetate synthesis reaction at the same conditions as Comparison B, with data shown as Example 5.

TABLE

|  | Performance at 100 Hours on Stream | | |
| --- | --- | --- | --- |
|  | % Vinyl Acetate Yield | % Vinyl Acetate Selectivity | % Oxygen Conversion |
| Comp. A | 63.9 | 63.9 | 100 |
| Ex. 1 | 68.1 | 68.6 | 99.6 |
| Ex. 2 | 66.5 | 66.5 | 100 |
| Comp. B | 47.5 | 71.6 | 66.3 |
| Ex. 3 | 50.4 | 74.1 | 68.0 |
| Ex. 4 | 50.7 | 73.5 | 69.0 |
| Ex. 5 | 50.6 | 74.9 | 67.6 |

Discussion of the Data

Data on yield, selectivity, and conversion, all based on oxygen, were obtained continuously during the length of these tests. For comparison, the performance data at one hundred hours elapsed time was calculated from a regression analysis of all of the data points.

The data show higher vinyl acetate yields and selectivity for the pretreated catalysts 1 and 2 versus Comparison A, and for pretreated catalysts 3, 4, and 5 versus Comparison B. Conversion remained about the same or slightly better.

The preferred embodiments and examples are intended to illustrate the invention. Other modifications can be made without departing from the scope of the invention, which is limited only by the following claims.

We claim:

1. A method for the pretreatment of a catalyst, the method comprising in sequence:

heating a virgin catalysts comprising metallic palladium and gold, for at least 15 minutes at a temperature at least sufficient to partially oxidize the palladium, in the presence of an oxidizing agent selected from the group consisting of oxygen, nitrogen oxides, nitrate salts, and hydrogen peroxide;

withdrawing the oxidizing agent and introducing an inert gas, and heating the catalyst at a temperature up to 500° C. for at least 15 minutes in the presence of a reducing agent selected from the group consisting of ammonia, carbon monoxide, aldehydes, alcohols, olefins, primary amines, and formic acid or salts thereof.

2. The method of claim 1 in which the inert gas is selected from the group consisting of nitrogen, carbon dioxide, helium, and argon.

3. The method of claim 1 in which the reducing agent is ethylene.

4. A palladium-gold catalyst composition which has been pretreated by the method of claim 1.

5. The method of claim 1 in which the catalyst is heated to a temperature above 100° C. in the presence of the reducing agent.

6. The method of claim 5 in which the catalyst is heated to a temperature from 150° to 350° C. in the presence of the reducing agent.

7. The method of claim 1 in which the reducing agent is introduced when the catalyst is at ambient temperature.

8. The method of claim 1 in which the oxidizing agent is an oxygen-containing gas.

9. The method of claim 8 in which the oxygen-containing gas is air.

10. The method of claim 1 in which the temperature of the catalyst in the presence of the oxidizing agent is from 125° to 500° C.

11. The method of claim 10 in which the temperature is from 150° to 350° C.

12. The method of claim 11 in which the temperature is from 200° to 300° C.

13. The method of claim 1 in which less than one weight percent of the palladium and gold are in a non-metallic form.

* * * * *